(12) United States Patent
Fredrickson et al.

(10) Patent No.: US 11,986,175 B2
(45) Date of Patent: May 21, 2024

(54) MEDICAL DEVICES FOR ENDOSCOPICALLY DISPENSING AGENTS AND RELATED METHODS OF USE

(71) Applicant: Boston Scientific Scimed, Inc., Maple Grove, MN (US)

(72) Inventors: Gerald Fredrickson, Westford, MA (US); Jennifer Whelehan, Westborough, MA (US); Matthew Laplaca, Franklin, MA (US); Lauren Lydecker, Millbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 642 days.

(21) Appl. No.: 17/095,276

(22) Filed: Nov. 11, 2020

(65) Prior Publication Data
US 2021/0145424 A1 May 20, 2021

Related U.S. Application Data

(60) Provisional application No. 62/936,765, filed on Nov. 18, 2019.

(51) Int. Cl.
*A61B 17/00* (2006.01)
*A61M 5/31* (2006.01)
(Continued)

(52) U.S. Cl.
CPC ..... *A61B 17/00491* (2013.01); *A61M 5/3129* (2013.01); *A61M 5/315* (2013.01);
(Continued)

(58) Field of Classification Search
CPC .... A61B 17/00491; A61B 2017/00495; A61B 2017/00893; A61B 17/12109; A61B 17/12186; A61B 2017/00884; A61B 2017/1205; A61B 2017/00522; A61B 2017/00889; A61B 2017/00951; A61B 1/00154; A61B 2017/00548;
(Continued)

(56) References Cited

U.S. PATENT DOCUMENTS 6,461,361 B1 10/2002 Epstein
6,699,214 B2 * 3/2004 Gellman ........... A61M 5/31596
604/82

(Continued)

FOREIGN PATENT DOCUMENTS

JP 2017533748 A * 11/2017 ....... A61B 17/00491
WO 00/15117 A1 3/2000
(Continued)

*Primary Examiner* — William R Carpenter
(74) *Attorney, Agent, or Firm* — Bookoff McAndrews PLLC (57) ABSTRACT

A medical system includes a propellant source containing a propellant fluid, containers containing a material, and a shaft having a plurality of lumens, each of the plurality of lumens having a first opening at a proximal end of the shaft and a second opening at a distal end of the shaft. The plurality of lumens are fluidly coupled to one or more of the propellant source and at least one of the plurality of containers, and a first lumen surrounds, is coaxial with, or is side-by-side with, at least one other lumen.

18 Claims, 4 Drawing Sheets

(51) Int. Cl.
*A61M 5/315* (2006.01)
*A61M 25/00* (2006.01)

(52) U.S. Cl.
CPC .... *A61M 25/0026* (2013.01); *A61M 25/0068* (2013.01); *A61B 2017/00495* (2013.01); *A61M 2025/0037* (2013.01); *A61M 2025/0039* (2013.01); *A61M 2202/02* (2013.01); *A61M 2202/04* (2013.01); *A61M 2202/064* (2013.01); *A61M 2210/1042* (2013.01)

(58) Field of Classification Search
CPC .. A61B 2017/00778; A61B 2017/2927; A61B 2218/003; A61M 25/0071; A61M 2025/0037; A61M 2025/0039; A61M 2025/0073; A61M 35/00; A61M 35/003; A61M 35/30; A61M 37/00; A61M 5/19; A61M 2202/02; A61M 2202/04; A61M 2202/064; A61M 25/0026; A61M 25/0068; A61M 31/00; A61M 5/00; A61M 5/3129; A61M 5/315; A61M 11/002; A61M 11/007; A61M 15/0003; A61M 2005/3128; A61M 2202/049; A61M 25/0028; A61M 25/0029; A61M 25/0032; A61M 25/0045; A61M 25/0097; A61M 5/007; A61M 5/1408; A61M 5/142; A61M 5/1452; A61M 5/2448; A61M 5/3134; A61M 5/31515; A61M 5/31596; A61M 5/44

See application file for complete search history.

(56) References Cited

U.S. PATENT DOCUMENTS

| | | | |
|---|---|---|---|
| 6,860,870 B2 * | 3/2005 | Pichon | B05B 7/066 604/82 |
| 8,152,755 B1 | 4/2012 | Wach et al. | |
| 9,700,290 B2 | 7/2017 | Hull et al. | |
| 2003/0209612 A1 | 11/2003 | Hahnen | |
| 2005/0123485 A1 * | 6/2005 | Suzuki | A61K 9/12 128/200.23 |
| 2006/0189944 A1 * | 8/2006 | Campbell | A61B 17/00491 604/191 |
| 2011/0245866 A1 | 10/2011 | Cassignham et al. | |
| 2016/0220239 A1 * | 8/2016 | Keene | A61B 10/04 |
| 2017/0119956 A1 * | 5/2017 | Leeflang | A61M 5/1407 |
| 2020/0093999 A1 * | 3/2020 | Neagos | B05B 7/265 |

FOREIGN PATENT DOCUMENTS

| | | | |
|---|---|---|---|
| WO | WO-03070110 A1 * | 8/2003 | ............ A61K 9/12 |
| WO | 2004/091688 A2 | 10/2004 | |
| WO | 2006/086479 A2 | 8/2006 | |
| WO | 2017/058338 A1 | 4/2017 | |

* cited by examiner

MEDICAL DEVICES FOR ENDOSCOPICALLY DISPENSING AGENTS AND RELATED METHODS OF USE

CROSS-REFERENCE TO RELATED APPLICATIONS

This application claims the benefit of priority from U.S. Provisional Application No. 62/936,765, filed on Nov. 18, 2019, which is incorporated by reference herein in its entirety.

TECHNICAL FIELD

The present disclosure relates generally to endoscopic medical devices and related methods of use. More particularly, in some embodiments, the disclosure relates to endoscopic medical tools and methods related to accessing target sites and dispensing fluids and/or agents to the target sites.

BACKGROUND

Medical tools for dispensing fluids and/or therapeutic agents to target tissue, for example to create a protective layer to minimize bleeds using adhesives, may include a catheter with a dispensing tip. Drawbacks of endoscopic systems using such tools include, for example, clogging of the dispensing tip by the adhesives, which generally cure quickly once mixed. Such clogging can prevent further dispensing of adhesive materials. The dispensing tip or the entire endoscope device may need to be replaced, which requires removable of the device from the patient. This increases procedure time and may result in the user losing track of the treatment site when the endoscopic device is reinserted into the patient. The present disclosure may solve one or more of these problems or other problems in the art. The scope of the disclosure, however, is defined by the attached claims and not the ability to solve a specific problem.

SUMMARY OF THE DISCLOSURE

A medical system including a propellant source configured to contain a propellant fluid, a plurality of containers each configured to contain a material, and a shaft having a plurality of lumens, each of the plurality of lumens having a first opening at a proximal end of the shaft and a second opening at a distal end of the shaft. The plurality of lumens are fluidly coupled to one or more of the propellant source and at least one of the plurality of containers, and a first lumen of the plurality of lumens surrounds, is coaxial with, or is side-by-side with, at least one other lumen from the plurality of lumens.

The propellant source may be fluidly coupled to each of the plurality of containers and to the first lumen.

The shaft may include a tip at the distalmost end of the shaft, the tip including structure for mixing contents within the shaft.

The tip may include a distal opening, a passage connecting at least one of the plurality of lumens of the shaft to the distal opening, and an auger rotatably disposed in the passage and may be configured to move material with the passage toward the distal opening.

The material in a first container of the plurality of containers may be a first agent, and the material in a second container of the plurality of containers may be a second agent, different from the first agent.

The propellant fluid may be a gas configured to mix with the first agent in the first container and mix with the second agent in the second container, and the gas may transmit each of the first agent and the second agent through a respective lumen of the plurality of lumens.

The first agent and the second agent may be configured to contact each other to form a mixture at or adjacent to a distal opening of the shaft, and at least one of an adhesive property, a viscosity, and a therapeutic property of the mixture may be greater than the adhesive property, the viscosity, and the therapeutic property, respectively, of each of the first agent and second agent.

The gas from the first lumen may be configured to atomize the mixture.

At least one of the plurality of containers may be a syringe. The syringe may include a barrel with an inlet at a proximal end of the barrel, an outlet at a distal end of the barrel, and a chamber between the inlet and the outlet, and a piston may be configured to be inserted into the inlet and to move relative to the barrel, wherein material within the chamber may be configured to be expelled from the outlet by moving the piston toward the outlet.

Each lumen of the plurality of lumens may be fluidly isolated from the other lumens of the plurality of lumens from the first opening of each lumen to the second opening of each lumen.

The propellant source may be fluidly coupled directly to the first lumen, wherein an inlet of each of the plurality of containers may be fluidly coupled to the propellant source and an outlet of each of the plurality of containers may be fluidly coupled to a respective lumen of the plurality of lumens at the proximal end of the shaft.

The plurality of lumens fluidly coupled to the plurality of containers may share a common wall, and wherein the first lumen surrounds the plurality of lumens may be fluidly coupled to the plurality of containers.

An actuator may be coupled to an outlet of the propellant source, the first lumen, and each of the plurality of containers, wherein the actuator may be configured to control a release of the propellant fluid from the propellant source.

The actuator may be configured to individually control the release of propellant fluid to each of the first lumen and a first container and a second container of the plurality of containers, and wherein the propellant fluid may be configured to aerosolize a mixture of a first material and a second material at the distal end of the shaft.

The propellant source may be fluidly coupled directly to an inlet of a first container of the plurality of containers, and the first container may be configured to contain a liquid. The propellant source may be fluidly coupled directly to an inlet of a second container of the plurality of containers, the second container may be configured to contain a powder, the propellant fluid may be configured to transmit the liquid through the first lumen and transmit the powder through a second lumen, the second lumen may be fluidly decoupled from the first lumen, the fluid and the powder may be configured to contact each other to form a mixture at or adjacent to a distal opening of the shaft, and wherein at least one of an adhesive property, a viscosity, and a therapeutic property may be greater than the adhesive property, the viscosity, and the therapeutic property, respectively, of each of the fluid and the powder.

A medical system including a propellant source configured to contain a propellant fluid, a plurality of containers each configured to contain a material, and a shaft having a plurality of lumens, each of the plurality of lumens having a first opening at a proximal end of the shaft and a second opening at a distal end of the shaft. The plurality of lumens are fluidly coupled to one or more of the propellant source and at least one of the plurality of containers, and a first lumen of the plurality of lumens surrounds, is coaxial with, or is side-by-side with, at least one other lumen from the plurality of lumens.

The propellant source may be fluidly coupled to each of the plurality of containers and to the first lumen.

The shaft may include a tip at the distalmost end of the shaft, the tip including structure for mixing contents within the shaft.

The tip may include a distal opening, a passage connecting at least one of the plurality of lumens of the shaft to the distal opening, and an auger rotatably disposed in the passage and may be configured to move material with the passage toward the distal opening.

The material in a first container of the plurality of containers may be a first agent, and the material in a second container of the plurality of containers may be a second agent, different from the first agent.

The propellant fluid may be a gas configured to mix with the first agent in the first container and mix with the second agent in the second container, and the gas may transmit each of the first agent and the second agent through a respective lumen of the plurality of lumens.

The first agent and the second agent may be configured to contact each other to form a mixture at or adjacent to a distal opening of the shaft, and at least one of an adhesive property, a viscosity, and a therapeutic property of the mixture may be greater than the adhesive property, the viscosity, and the therapeutic property, respectively, of each of the first agent and second agent.

The gas from the first lumen may be configured to atomize the mixture.

At least one of the plurality of containers may be a syringe. The syringe may include a barrel with an inlet at a proximal end of the barrel, an outlet at a distal end of the barrel, and a chamber between the inlet and the outlet, and a piston may be configured to be inserted into the inlet and to move relative to the barrel, wherein material within the chamber may be configured to be expelled from the outlet by moving the piston toward the outlet.

Each lumen of the plurality of lumens may be fluidly isolated from the other lumens of the plurality of lumens from the first opening of each lumen to the second opening of each lumen.

The propellant source may be fluidly coupled directly to the first lumen, wherein an inlet of each of the plurality of containers may be fluidly coupled to the propellant source and an outlet of each of the plurality of containers may be fluidly coupled to a respective lumen of the plurality of lumens at the proximal end of the shaft.

The plurality of lumens fluidly coupled to the plurality of containers may share a common wall, and wherein the first lumen surrounds the plurality of lumens may be fluidly coupled to the plurality of containers.

An actuator may be coupled to an outlet of the propellant source, the first lumen, and each of the plurality of containers, wherein the actuator may be configured to control a release of the propellant fluid from the propellant source.

The actuator may be configured to individually control the release of propellant fluid to each of the first lumen and a first container and a second container of the plurality of containers, and wherein the propellant fluid may be configured to aerosolize a mixture of a first material and a second material at the distal end of the shaft.

The propellant source may be fluidly coupled directly to an inlet of a first container of the plurality of containers, and the first container may be configured to contain a liquid. The propellant source may be fluidly coupled directly to an inlet of a second container of the plurality of containers, the second container may be configured to contain a powder, the propellant fluid may be configured to transmit the liquid through the first lumen and transmit the powder through a second lumen, the second lumen may be fluidly decoupled from the first lumen, the fluid and the powder may be configured to contact each other to form a mixture at or adjacent to a distal opening of the shaft, and wherein at least one of an adhesive property, a viscosity, and a therapeutic property may be greater than the adhesive property, the viscosity, and the therapeutic property, respectively, of each of the fluid and the powder.

A medical system including a propellant source containing a propellant gas, a first container fluidly coupled to the propellant source and containing a powdered agent, a second container fluidly coupled to the propellant source and containing a fluid, and a shaft having a first lumen fluidly coupled to the first container, a second lumen fluidly coupled to the second container, and a third lumen fluidly coupled to the propellant source, wherein the propellant gas propels the powdered agent through the first lumen, and propels the fluid through the second lumen, so that the fluid mixes with the powdered agent distal to distal openings of the first and second lumens.

A first material may be flowed through a first lumen of a shaft, via a propellant fluid, a second material, different from the first material, may be flowed through a second lumen of the shaft, via the propellant fluid, wherein the first lumen may be coaxial with, side-by-side with, or surrounds the second lumen, and a mixture of the first material and the second material may be applied to tissue adjacent to a distalmost end of the shaft.

The shaft may be inserted in a natural orifice of a body, the shaft may be advanced to a target site of a gastrointestinal (GI) of the body, and the mixture may be applied to tissue at the target site.

The mixture may be configured to adhere to the tissue of the GI tract, and the material may include a therapeutic agent.

The propellant gas may be flowed through a third lumen of the shaft, surrounding the first and second lumens, wherein applying the mixture may include aerosolizing the mixture with the propellant gas at or adjacent to the distalmost end of the shaft.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

The present disclosure is described with reference to exemplary medical systems and medical tools for accessing a target site and dispensing one or more agents, for example, a plurality of fluids that, once mixed, form an adhesive gel or liquid and/or regenerative agent. Such agents or fluids may minimize delayed bleeds in a patient. However, it should be noted that reference to any particular procedure and/or any particular agent is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer to exact and approximate shapes.

Figure 1:
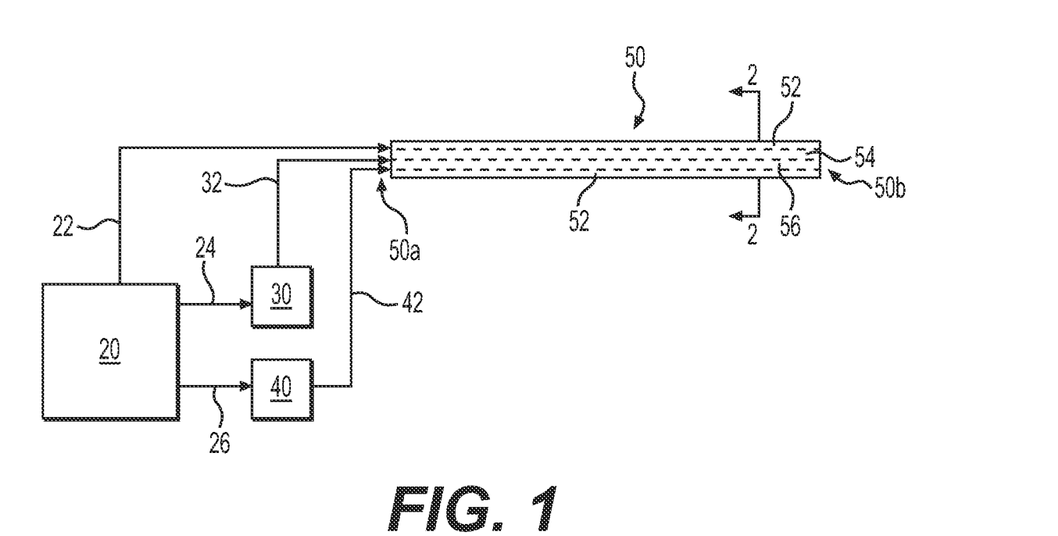
FIG. 1 is a schematic view of a medical system according to an embodiment.

Referring to FIG. 1, a medical system 10 according to an embodiment is shown. Medical system 10 includes a propellant fluid containment device 20, a first container 30 and a second container 40 for containing first and second agents, respectively, and a catheter 50 (e.g., a shaft). These elements may be directly connected, or may be connected by tubes, hoses, valves, or the like, as will be described herein.

Containment device 20 is configured to contain a propellant fluid, such as a gas, e.g., carbon dioxide or any other gas or fluid known in the art for dispensing material, such as a medical powder or reagent, into a patient at a target location. While shown as a polygonal container, containment device 20 may be any shape, such as a sphere, or any other shape known in the art for containing gas. For example, containment device 20 may be a carbon dioxide tank or cylinder typically found in medical settings, such as a hospital, and may be connected to various components of medical system 10 by one or more conduits, as will be described herein. Containment device 20 may include one or more outer walls defining one or more inner chambers (not shown), the inner chamber(s) configured to contain the propellant fluid. The walls of containment device 20 may be formed of any material suitable for containing the propellant fluid, such as but not limited to a metal alloy, a ceramic, or other material known in the art. The propellant fluid contained in the inner chamber of containment device 20 may be under pressure. Accordingly, the walls are formed of a material and/or a thickness suitable to contain the propellant fluid at a pressure of, for example, approximately 5 pounds per square inch (PSI) to approximately 40 PSI, but is not limited thereto. For example, gases which may be contained in containment device 20 include $CO_2$ or other like gases for propelling material from a medical device and into a body. It will be understood that these gases are examples and are not limiting to the types of gases contained in containment device 20.

With continued reference to FIG. 1, containment device 20 is fluidly connected to catheter 50 via a first conduit 22, fluidly connected to first container 30 via a second conduit 24, and fluidly connected to second container 40 via a third conduit 26. While not shown, containment device 20 may include one or more actuators and valves for controlling the release of the propellant fluid to each of first conduit 22, second conduit 24, and third conduit 26. Alternatively, or additionally, an actuation device (such as the actuation device described in FIG. 5) may be used to control the release of propellant fluid from containment device 20. As will be understood by one of ordinary skill in the art, modifying the amount of propellant fluid released from containment device 20 to each of first and second containers 30, 40 may change the mixture ratio of the fluids, solids, or agents contained in first container 30 and second container 40, and/or may change the discharge rate of the final mixture from catheter 50, as will be explained in greater detail herein. Additionally, or alternatively, one or more pressure regulators may be associated with one or more of containment device 20, first, second, and third conduits 22, 24, 26, or first and second containers 30, 40. The pressure regulators may maintain an appropriate pressure of propellant gas through medical system 10. It will be understood that first, second, and third conduits 22, 24, 26, and other conduits described herein, may be any material known for transmitting materials used in a medical setting. These conduits may be rigid or flexible, according to a desired application.

As further shown in FIG. 1, first container 30 and second container 40 are downstream of containment device 20. First container 30 and second container 40 may have similar or different characteristics, e.g., shapes, sizes, or the like. First container 30 and second container 40 may each contain one or more agents, in the form of a fluid or a solid (including particles), which, once mixed together, are activated to have additional properties, e.g., an adhesive, to treat a target site. First container 30 and second container 40 may be formed of any material known in the art for containing therapeutic agents or other fluids or solids for delivery to the human body. For example, the materials used to form first and second containers 30, 40 may be chemically inert to the one or more agents contained therein. In addition, first container 30 and second container 40 may be designed to withstand a pressure of propellant gas transmitted from containment device 20 to each of first container 30 and second container 40. Additionally, one or more of first container and second container 30, 40 may have fins or other protrusions within the container to aid in mixing of the propellant gas and the one or more agents to produce a uniform mixture at a downstream outlet of each of first container 30 and second container 40. While only two containers are shown in FIG. 1, it will be understood that any number of containers may be included in medical system 10 as appropriate, based on the number of agents, solvents, or other fluids or solids, being transmitted by catheter 50.

As further shown in FIG. 1, the downstream outlets of first container 30 and second container 40 are connected to catheter 50 by fourth conduit 32 and fifth conduit 42, respectively. Fourth conduit 32 and fifth conduit 42 each transport a mixture of the contents of the respective container and the propellant fluid from containment device 20.

Each mixture enters a separate lumen at a proximalmost end 50a of catheter 50, as will be described herein. As explained herein, regulators may be used to modify the pressure of the propellant fluid and/or a mixture of the propellant fluid with any of the agents described herein. For example, one or more regulators may be operably associated with the downstream outlets of one or more of the first container 30 or the second container 40 and/or one or more of the fourth conduit 32 and the fifth conduit 42.

As will be understood, each of containment device 20, first container 30, and second container 40 may be stand-alone elements, e.g., containment tanks found in a hospital or other medical setting. Alternatively, one or more of the containers may be attached to or contained within a housing and associated with, e.g., an actuation device, such as the actuation device described in FIG. 5. In this manner, medical system 10 may be handheld or portable.

Figure 2:
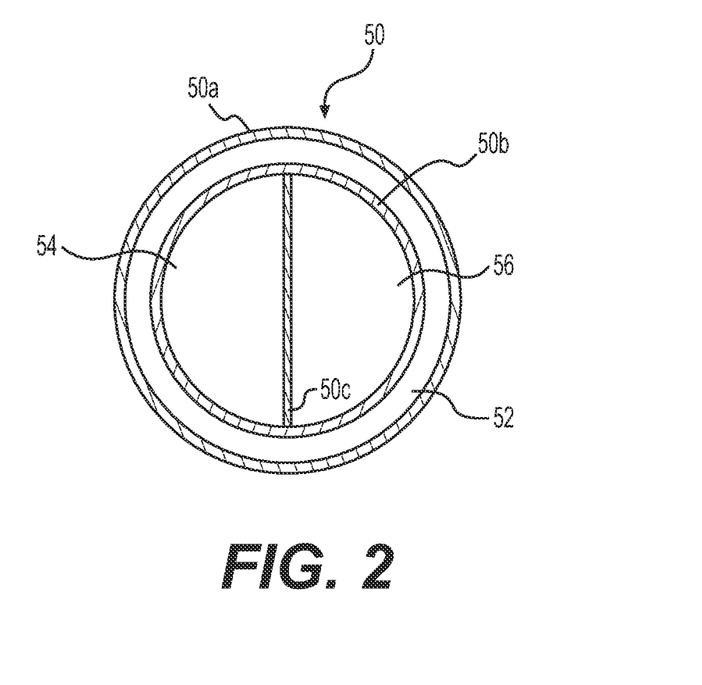
FIG. 2 is a cross-section of a medical device of the medical system of FIG. 1 along the line 2-2, according to an embodiment.

Referring to FIG. 2, a cross-section of catheter 50 is shown, taken along the line 2-2 of FIG. 1. Catheter 50 may be a shaft (e.g., a flexible sheath, catheter, tube, or the like) and includes a second lumen 54 and a third lumen 56, each fluidly separated from each other. A first lumen 52, fluidly separated from second and third lumens 54, 56, is defined by an outermost wall 50b of second and third lumens 54, 56 and an outermost wall 50a of catheter 50, and surrounds second and third lumen 54, 56. As shown in FIG. 2, second and third lumen 54, 56 share a common wall 50c, resulting in a semicircular shaped cross-section for each of lumen 54 and 56, but it will be understood that the invention is not limited to this example. For example, second and third lumen 54, 56 may be independent tubes disposed within catheter 50, with a space separating these independent tubes, and that space may be fluidly coupled with first lumen 52. For example, second and third lumens 54, 56 may be discrete tubes having circular or other cross-sectional shapes. While not shown, second lumen 54 and/or third lumen 56 may be attached to an outer wall of catheter 50 by one or more protrusions, adhesives, or other means, to maintain a proper spacing between and position of the second and third lumens 54, 56 relative to the outer wall of catheter 50. Further, any of first, second, and third lumens 52, 54, 56 may extend to distalmost end 50b of catheter 50. Alternatively, one or more of first, second, or third lumen 52, 54, 56 may terminate proximal to distalmost end 50b of catheter 50.

As will be explained in greater detail herein, propellant fluid from first lumen 52 may mix with or otherwise come into contact with the reagent and propellant fluid mixtures from second and third lumens 54, 56, respectively, at a distalmost end 50b of catheter 50 (see FIG. 1). Once this occurs, the chemical properties of the mixtures may change to produce, e.g., an adhesive mixture. Additionally, or alternatively, the combined mixtures, after the fluids, reagents, etc., exit at distalmost end 50b, may activate a reagent, such as an antibacterial or other reagent, or the reagent may already be activated in one or both of the mixtures emanating from first and second containers 30, 40. Additional physical properties of the mixture resulting from contact/mixing after exiting from distalmost end 50b may be different from physical properties of the reagents or other fluids or mixtures exiting from first and second containers 30, 40. For example, the resulting mixture may be more viscous, may be an adhesive, may be a gel, and/or may activate a therapeutic agent.

A method of operation of medical system 10 will now be explained. Catheter 50 is inserted into a patient and advanced to a target site. Catheter 50 may be inserted directly into the patient without use of a guiding device, or catheter 50 may be advanced along an endoscope, guidewire, or other like device that has been previously advanced to the target site. Catheter 50 may be inserted through a natural orifice, like the mouth, anus, or the like, or through a surgical incision in the body. Once a distalmost tip of catheter, e.g., distalmost end 50b, is positioned at the target site, a user may actuate one or more actuators associated with containment device 20 and/or medical system 10 generally to release propellant gas from container 20 into one or more of first conduit 22, second conduit 24, and third conduit 26. The one or more actuators allow the user to control the amount of propellant fluid flowing in each of first, second, and third lumen 22, 24, and 26, and thereby control the dispersal rate of the reagents or other fluids or solids in first and second containers 30, 40. The propellant gas enters first and second containers 30, 40 and mixes with the reagents, fluids, or solids therein. According to an example, a first mixture of a first reagent and the propellant gas travels from first container 30 to second lumen 54 via fourth conduit 32. Similarly, a second mixture of a second reagent and the propellant gas may travel from second container 40 to third lumen 56 via fifth conduit 42.

The first mixture and the second mixture subsequently exit second lumen 54 and third lumen 56, respectively, at distal end 50b of catheter 50. The first mixture and the second mixture mix with and, in some embodiments, may be atomized by propellant fluid from first lumen 52. According to an example, mixing the first and the second mixtures after exiting distalmost end 50b may cause this resulting mixture to be activated or crosslinked, e.g., to create a gel or liquid adhesive, which may adhere to the target site, and/or may activate one or more therapeutic in the resulting mixture. As the mixture is dispersed from distal end 50b of catheter 50, catheter 50 may be moved relative the target site to deposit the resulting mixture to the target site. In this manner, the first mixture and the second mixture have no contact within catheter 50, thereby preventing the mixture from becoming an adhesive within catheter 50 and preventing the adhesive from curing within and full or partially blocking the outlet of catheter 50 at distal end 50b.

It will be understood that first container 30 and second container 40 may be eliminated from system 10 if catheter 50 is preloaded with the agent, fluid, or solid that is otherwise in first and second containers 30, 40. For example, second lumen 54 and third lumen 56 may be preloaded with different agents. According to an example, containment device 20 may be directly connected to catheter 50 without any intervening containers. In this example, containment device 20 may provide propellant gas directly to first, second, and third lumens 52, 54, 56, forcing the first and second agents down respective second and third lumens 54, 56 and, for example, atomizing the mixture of the first and second agents at distalmost end 50b of catheter 50 with propellant gas from first lumen 52. This may reduce the size of medical system 10 and allow for greater portability, and may provide a more even and/or complete distribution of the agent at the target site. Alternatively, or additionally, first and second containers 30, 40 may be attached to respective second and third lumens 54, 56 if a user determines that additional first and second agents are necessary to be dispersed to the target site. According to an example, each element of system 10 may be screw fit, snap fit, or the like to other elements to enable quick, efficient, and safe addition or removal of elements. In this way, containment device 20 may be disconnected from second and third lumens 54, 56, and first and second containers 30, 40 may be interposed between containment device 20 and respective second and third lumens 54, 56.

Figure 3:
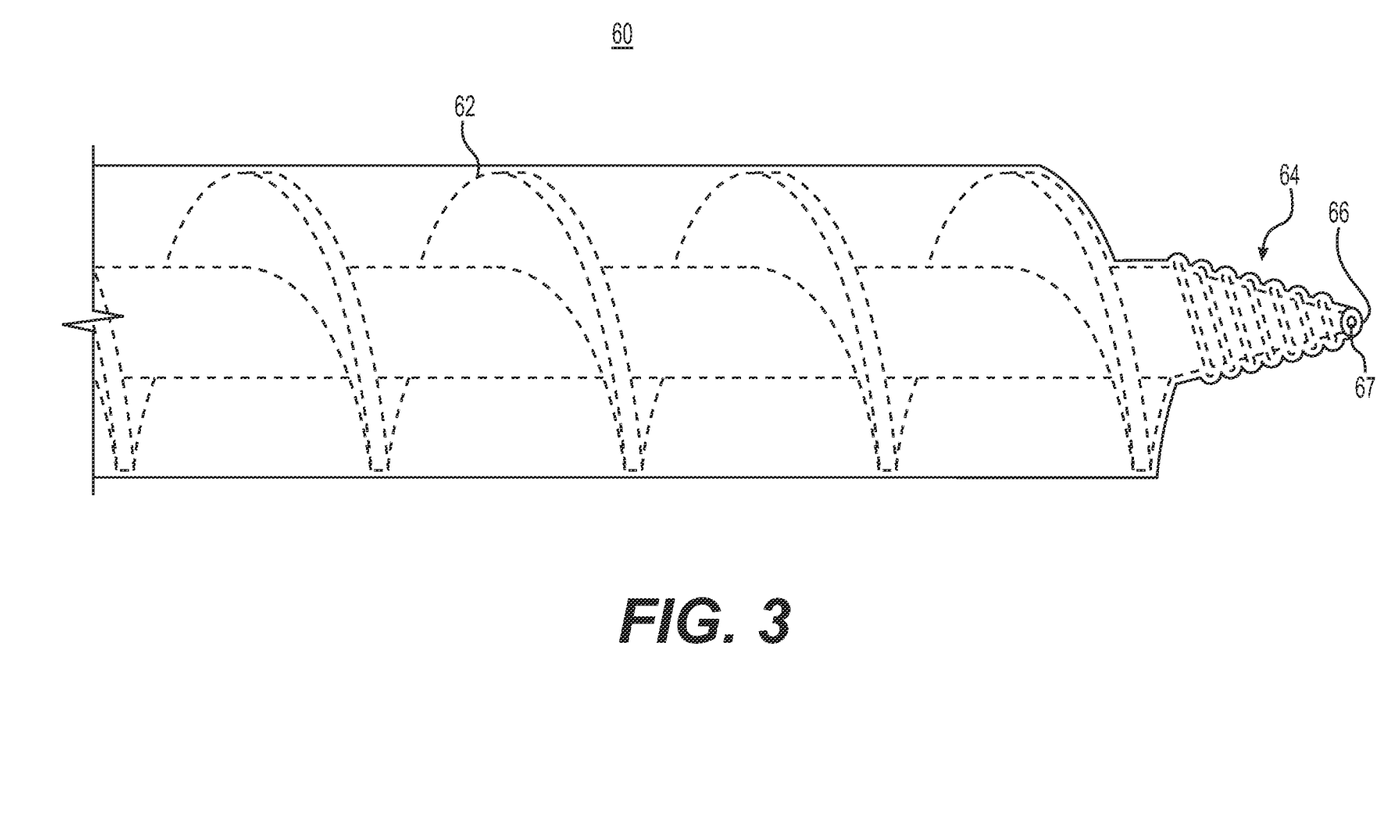
FIG. 3 is a catheter tip for use with the medical system of FIG. 1, according to an embodiment.

A catheter tip 60 according to an embodiment is shown in FIG. 3. Catheter tip 60 may include an auger 62 for moving and/or mixing one or more of the first mixture and the second mixture toward an outlet 67 (or a plurality of outlets) at distalmost end 66. Catheter tip 60 may include a tapered portion 64 which tapers toward distalmost end 66. Catheter tip 60 may be integrally formed with catheter 50 or may be attached to distalmost end 50b of catheter 50 by, e.g., an adhesive, a snap-fit connection, or the like. Catheter tip 60 may be permanently fixed to, or may be removably attached to, catheter 50. Catheter tip 60 may dispense the mixture of agents with or without atomization of the agents. For example, auger 62 may move the combined first mixture and second mixture from each of second lumen 54 and third lumen 56 at the distalmost end 50b of catheter 50 toward distalmost end 66, and the combined mixture may be dispensed to the target site without atomizing the combined mixture. Alternatively, the combined mixture may be moved toward distalmost end 66 of catheter tip 60, and propellant gas from first lumen 52 may atomize and propel the combined mixture from catheter 50 (via catheter tip 60) toward the target site.

As shown in FIG. 3, auger 62 may include a single helical thread, where the diameter and/or pitch of the thread decreases at tapered portion 64 of catheter tip 60, which may increase the precision of the distribution of the agent from catheter tip 60 to the target site. Auger 62 is not limited to a single thread, nor is auger 62 limited to a thread size and/or pitch. Additionally, auger 62 may include protrusions or thread surfaces that cause agents therein to be mixed during dispersal. Auger 62 may be driven by any way known, including but not limited to electrical or pneumatic driving.

Figure 4:
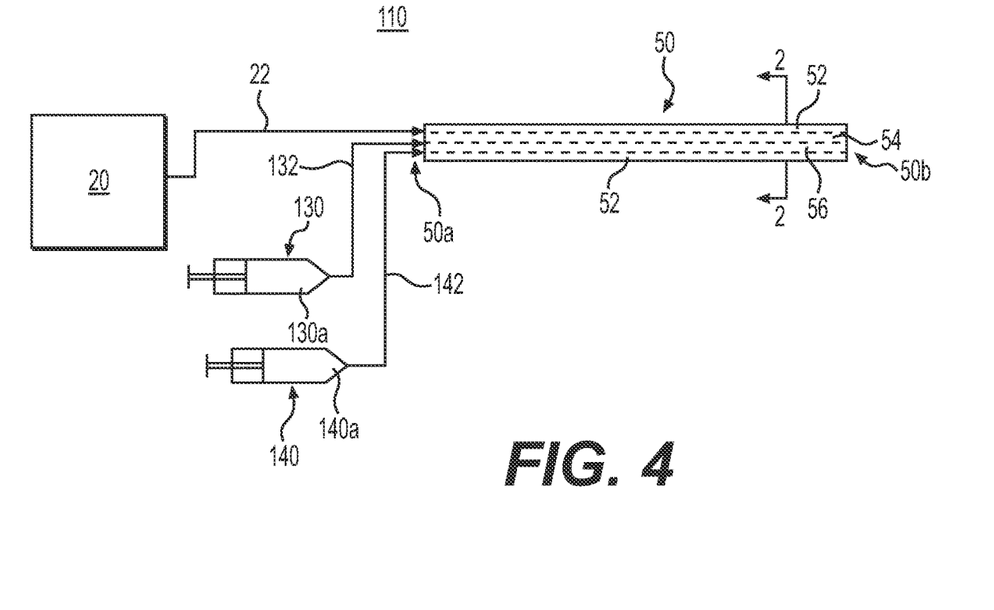
FIG. 4 is a schematic view of another example of a medical system, according to an embodiment.

Referring to FIG. 4, a medical system 110 according to another example is illustrated. Containment device 20, first conduit 22, and catheter 50 have similar features as those devices in medical system 10 of FIG. 1. According to an example, a first syringe 130 contains a first fluid, agent, or other material in a first chamber 130a, and a second syringe 140 contains a second fluid, agent, or other material in a second chamber 140a. First and second syringes 130, 140 may be any known syringes used in medical systems, including a piston for forcing material from respective first and second chambers 130a, 140a out of a distalmost end of a body, or barrel, of the syringe. First and second chambers 130a, 140a of respective first and second syringes 130, 140 may be filed with materials, e.g., agents, therapeutic agents, or the like, by removing the pistons, adding the material, and reinserting the pistons. Alternatively, or additionally, first and second syringes 130, 140 may be filled through a distalmost end thereof by creating a vacuum in first and second chambers 130a, 140a by pulling the pistons proximally.

Actuation of syringe 130 by, for example, forcing the plunger into the body/barrel, causes the first agent in first chamber 130a to flow through a second conduit 132 to second lumen 54. Similarly, actuation of syringe 140 causes the second agent in second chamber 140a to flow through a third conduit 142 to third lumen 56. First syringe 130 and second syringe 140 may be individually or simultaneously activated. Further, first and second syringes 130, 140 may be actuated by a user, e.g., pushing with a hand or finger, on a proximalmost end of the plunger of first and second syringes 130, 140. Alternatively, or additionally, first and second syringes 130, 140 may be actuated pneumatically or using a mechanical or electrical device for depressing the pistons of each of first and second syringes 130, 140. For example, the pistons of each of first and second syringes 130, 140 may be connected to a device having a motor, e.g., an electrically driven motor, that may separately or simultaneously actuate the pistons of each of the first and second syringes 130, 140. The device may further include a processor and a memory having a program stored thereon that may control the motor to actuate the first and second syringes 130, 140.

First and second agents of medical system 110 may be dispersed from distal end 50b of catheter 50 by, e.g., atomizing a mixture of first and second agents using propellant gas. For example, as discussed above, first lumen 52 may be arranged about second and third lumens 54, 56 and may receive propellant gas from containment device 20 via first conduit 22. The propellant gas may force a combined mixture of first and second agents from distalmost end 50b of catheter 50. Alternatively, the mixing catheter tip 60 of FIG. 3 may be used to dispense a combined mixture of first and second agents, as described herein.

Figure 5:
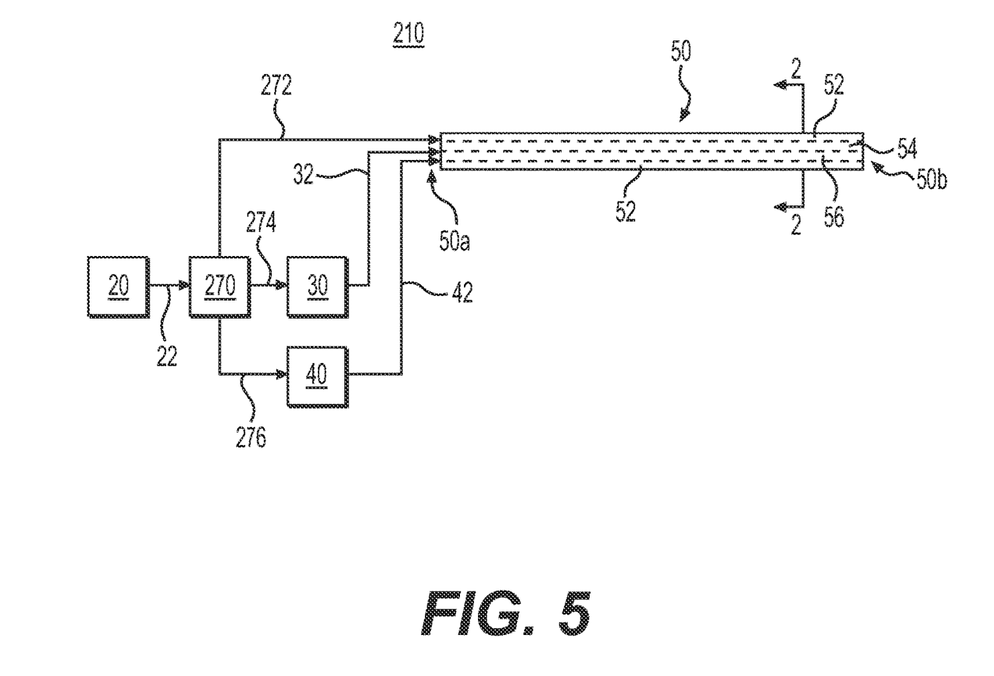
FIG. 5 is a schematic view of another example of a medical system, according to an embodiment.

Referring to FIG. 5, another example of a medical system 210 is shown. Medical system 210 includes similar features of medical system 10 of FIG. 1. As shown in FIG. 5, containment device 20 is attached to an actuation mechanism 270 via first conduit 22. Actuation mechanism 270 may be a console, trigger mechanism, or the like, having one or more actuation elements for fluidly coupling containment device 20 to elements downstream of actuation mechanism 270, such as first and second containers 30, 40. Actuation mechanism 270 is connected to first lumen 52 via a second conduit 272, connected to first container 30 via third conduit 274, and connected to second container 40 via fourth conduit 276. Actuation mechanism 270 may include a valve, discrete fluid passages, and/or other actuation devices for controlling the release of fluid to each of conduits 272, 274, and 276. Actuation mechanism 270 allows a user to control the amount of propellant fluid released to each of first lumen 52, first container 30, and second container 40. Controlling the propellant fluid allows the user to control the amount of first and second agents released from distalmost end 50b of catheter 50 and the rate at which the propellant gas is released from first lumen 52 at distalmost end 50b. Actuation mechanism 270 may additionally include a processor and a memory having one or more programs stored thereon that may automatically actuate actuation mechanism 270 to disperse propellant fluid from containment device 20.

Figure 6:
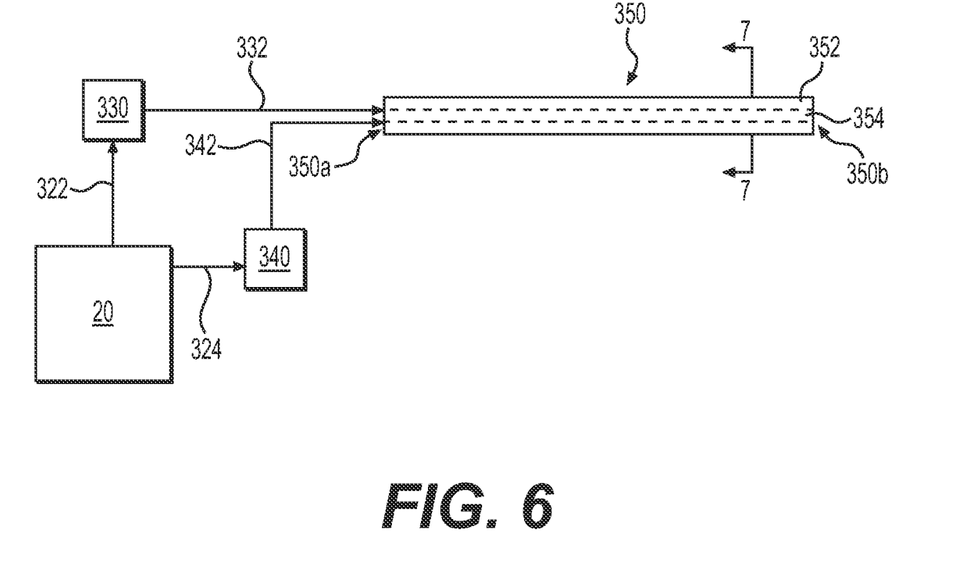
FIG. 6 is a schematic view of another example of a medical system, according to an embodiment.

A medical system 310 according to another embodiment is shown in FIG. 6. Medical system 310 includes containment device 20 fluidly coupled to a first container 330 and a second container 340 via first and second conduits 322, 324 respectively. First container 330 may include a fluid, such as saline, but is not limited thereto. Second container 340 may include one or more agents, e.g., a powdered agent or mixture of powdered agents, which may be activated once contacted by a fluid, such as saline, or any other medically suitable fluid, which is stored in first container 330.

First container 330 is fluidly coupled to a proximalmost end 350a of catheter 350 via a third conduit 332. Second container 340 is similarly fluidly coupled to proximalmost end 350a of catheter 350 via a fourth conduit 342. Both first lumen and second lumen 352, 354 extend from proximalmost end 350a of catheter 350 to a distalmost end 350b, but one or both of first and second lumen 352, 354 may terminate proximally of distalmost end 350b. It will be understood that the arrangement is not limited, and first container 330 may be fluidly coupled to second lumen 354, while second lumen may be fluidly coupled to first lumen 352.

Figure 7:
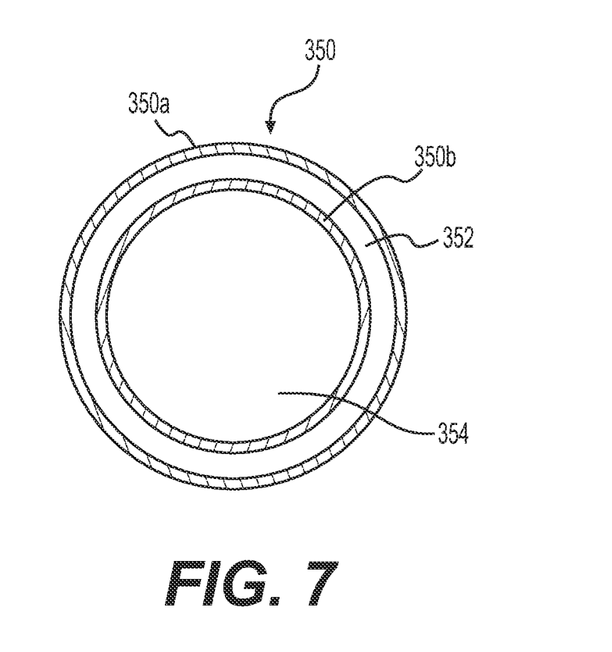
FIG. 7 is a cross-section of a medical device of the medical system of FIG. 6 along the line 7-7, according to an embodiment.

With reference to FIG. 7, a cross-section of catheter 350 taken along the line 7-7 in FIG. 6 is shown. First lumen 352 is coaxially arranged with second lumen 354, and first lumen 352 is defined by an outermost wall 350b of second lumen 354 and an outermost wall 350 a of catheter 350. As discussed herein, a mixture of fluid and propellant gas from first container 330 may be transmitted along first lumen 352, and one or more agents from second container 340 may be transmitted along second lumen 354 by the propellant gas. Alternatively, the one or more agents from second container 340 may be transmitted along first lumen 352 and the propellant gas and fluid mixture may be transmitted along second lumen 354. In both configurations, the propellant gas and fluid mixture may atomize the one or more agents at distalmost end 350*b* of catheter 350. This interaction may support mixing of the powdered agent(s), causing the one or more agents to be crosslinked or activated and to be propelled toward a treatment site. This also minimizes cloud formation during the application of the powdered agent(s) during application to the target site. While only one lumen, second lumen 354, is shown for transferring the powdered agent(s), the invention is not limited, and multiple containers and/or lumens may be used. Additionally, the powdered agent(s) may be urged down a lumen of the catheter in any manner described herein.

While different medical systems have been described, it will be understood that the particular arrangements of elements in these medical systems are not limited. Moreover, a size and a shape of the catheter or shaft of the medical system, or the dispersal method of the medical system, are not limited. As described in examples herein, agents, such as fluids or powders, are dispersed from a distal end of a catheter, where the agent(s) interact with each other or an additional substance to change one or more physical properties thereof. In this manner, a therapeutic agent, such as an adhesive to limit bleeds, may be applied endoscopically without clogging lumens, passages, inlets, or outlets of the medical system.

It will be apparent to those skilled in the art that various modifications and variations can be made to the disclosed device without departing from the scope of the disclosure. For example, the configuration of the containers, including the propellant containment device, the shaft and the lumen therein, and/or the agent(s) may be modified to provide a desired medical therapy. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:

a propellant source configured to contain a propellant fluid;

a plurality of containers each configured to contain a material; and a shaft comprising:

a plurality of lumens, each of the plurality of lumens having a first opening at a proximal end of the shaft and a second opening at a distal end of the shaft, the plurality of lumens are fluidly coupled to one or more of the propellant source and at least one of the plurality of containers, and a tip at a distalmost end of the shaft, the tip comprising:

a distal delivery opening, a passage connecting at least one of the plurality of lumens of the shaft to the distal delivery opening, and an auger extending to the distal delivery opening, rotatably disposed in the passage, and configured to move material within the passage toward the distal delivery opening, wherein the auger is configured to mix contents within the shaft; and wherein a first lumen of the plurality of lumens surrounds, is coaxial with, or is side-by-side with, at least one other lumen from the plurality of lumens.

2. The medical system according to claim 1, wherein the propellant source is fluidly coupled to each of the plurality of containers and to the first lumen.

3. The medical system according to claim 1, wherein the material in a first container of the plurality of containers is a first agent, and wherein the material in a second container of the plurality of containers is a second agent, different from the first agent.

4. The medical system according to claim 3, wherein the propellant fluid is a gas configured to mix with the first agent in the first container and mix with the second agent in the second container, and wherein the gas is configured to transmit each of the first agent and the second agent through a respective lumen of the plurality of lumens.

5. The medical system according to claim 4, wherein the gas from the first lumen is configured to atomize the mixture.

6. The medical system according to claim 1, wherein at least one of the plurality of containers is a syringe, wherein the syringe includes:

a barrel with an inlet at a proximal end of the barrel, an outlet at a distal end of the barrel, and a chamber between the inlet and the outlet; and a piston configured to be inserted into the inlet and to move relative to the barrel, wherein material within the chamber is configured to be expelled from the outlet by moving the piston toward the outlet.

7. The medical system according to claim 1, wherein each lumen of the plurality of lumens is fluidly isolated from the other lumens of the plurality of lumens from the first opening of each lumen to the second opening of each lumen.

8. The medical system according to claim 1, wherein the propellant source is fluidly coupled directly to the first lumen, wherein an inlet of each of the plurality of containers is fluidly coupled to the propellant source and an outlet of each of the plurality of containers is fluidly coupled to a respective lumen of the plurality of lumens at the proximal end of the shaft.

9. The medical system according to claim 1, wherein the plurality of lumens fluidly coupled to the plurality of containers share a common wall, and wherein the first lumen surrounds the plurality of lumens fluidly coupled to the plurality of containers.

10. The medical system of claim 9, wherein the plurality of lumens includes a second lumen and a third lumen, wherein the common wall is positioned between the second lumen and the third lumen so that a cross section of each of the second lumen and the third lumen has a semi-circle shape.

11. The medical system of claim 10, wherein a combined perimeter of the second lumen and the third lumen forms a first circle, wherein a perimeter of the first lumen forms a second circle concentric with the first circle.

12. The medical system according to claim 1, further comprising an actuator coupled to an outlet of the propellant source, the first lumen, and each of the plurality of containers, wherein the actuator is configured to control a release of the propellant fluid from the propellant source.

13. The medical system according to claim 12, wherein the actuator is configured to individually control the release of propellant fluid to each of the first lumen and a first container and a second container of the plurality of containers, and wherein the propellant fluid is configured to aerosolize a mixture of a first material and a second material at the distal end of the shaft.

14. The medical system of claim 1, wherein the auger includes a helical thread, the helical thread including a pitch and a diameter, wherein the tip includes a tapered portion tapering towards the distalmost end of the shaft, and the auger includes a tapered portion at a distal end of the auger, wherein the tapered portion of the auger is positioned within the tapered portion of the tip.

15. The medical system of claim 14, wherein the diameter of the helical thread decreases along the tapered portion of the auger towards the distalmost end of the shaft, wherein a pitch of the helical thread at the tapered portion of the auger is less than a pitch of the helical thread along a proximal portion of the auger.

16. A medical system, comprising:

a propellant source configured to contain a propellant fluid;

a plurality of containers each configured to contain a material; and a shaft comprising:

a tip at a distalmost end of the shaft, the tip including an auger therein for mixing contents within the shaft, a plurality of lumens, each of the plurality of lumens having a first opening at a proximal end of the shaft and a second opening at a distal end of the shaft, wherein the plurality of lumens includes a first lumen fluidly coupled to the propellant source, a second lumen coupled to a first container of the plurality of containers, and a third lumen coupled to a second container of the plurality of containers, wherein the second lumen and the third lumen share a common wall so that a cross section of each of the second lumen and the third lumen has a semi-circle shape, and the first lumen surrounds the second lumen and the third lumen, wherein the auger includes a helical thread, the helical thread including a pitch and a diameter, wherein the tip includes a tapered portion, and the auger includes a tapered portion at a distal end of the auger, wherein the tapered portion of the auger is positioned within the tapered portion of the tip so as to extend to a distal delivery opening of the tip.

17. The medical system of claim 16, wherein the diameter of the helical thread decreases along the tapered portion of the auger towards the distalmost end of the shaft, wherein a pitch of the helical thread at the tapered portion of the auger is less than a pitch of the helical thread along a proximal portion of the auger.

18. The medical system of claim 17, wherein the first lumen is annular.

* * * * *